(12) United States Patent
Berg

(10) Patent No.: US 7,237,677 B2
(45) Date of Patent: Jul. 3, 2007

(54) MIRRORED ORAL-PRODUCT CONTAINER

(76) Inventor: Robert I. Berg, 8435 Seafair Ct., Blaine, WA (US) 98230

( * ) Notice: Subject to any disclaimer, the term of this patent is extended or adjusted under 35 U.S.C. 154(b) by 281 days.

(21) Appl. No.: 10/858,391

(22) Filed: Jun. 2, 2004

(65) Prior Publication Data

US 2006/0157378 A1    Jul. 20, 2006

Related U.S. Application Data

(60) Provisional application No. 60/511,298, filed on Oct. 16, 2003.

(51) Int. Cl.
*B65D 71/00*    (2006.01)

(52) U.S. Cl. .......................... 206/581; 206/37; 206/235

(58) Field of Classification Search ............ 206/37–39, 206/235, 581; 132/287, 294, 301, 304, 316; 220/252, 345.2, 345.4
See application file for complete search history.

(56) References Cited

U.S. PATENT DOCUMENTS

| | | | |
|---|---|---|---|
| 1,672,417 A | 6/1928 | Leberman | |
| 1,695,477 A | 12/1928 | Zeindlhofer | |
| 1,709,182 A | 4/1929 | McKnight et al. | |
| 2,178,188 A | 10/1939 | Schmidt | |
| 2,196,801 A | 4/1940 | Kreisler | |
| 2,309,111 A | 1/1943 | Hotersall | |
| 2,362,120 A | 11/1944 | De Swart | |
| 2,393,568 A | 1/1946 | Root | |
| 2,479,854 A | 8/1949 | Miller | |
| 2,489,525 A | 11/1949 | Crane | |
| 3,442,414 A | 5/1969 | Pelli | |
| 3,894,550 A | 7/1975 | Eaton | |
| 3,921,649 A * | 11/1975 | Milbrath | 132/308 |
| 4,337,859 A * | 7/1982 | Murphy et al. | 206/37 |
| 4,421,127 A * | 12/1983 | Geer | 132/294 |
| 4,518,092 A | 5/1985 | Contreras, Sr. | |
| 4,589,431 A | 5/1986 | Yuhara | |
| 4,799,503 A | 1/1989 | Tahara | |
| 4,819,829 A * | 4/1989 | Rosten et al. | 220/345.3 |
| 4,932,547 A * | 6/1990 | Rodriguez | 206/38 |
| 5,163,457 A * | 11/1992 | Lombardi, Jr. | 132/304 |
| 5,205,431 A | 4/1993 | Zinnbauer | |
| 5,476,194 A | 12/1995 | Hippely | |
| 5,611,362 A | 3/1997 | Duncan et al. | |
| 5,638,838 A | 6/1997 | Lombardi | |
| 5,680,933 A | 10/1997 | Miller | |
| 5,842,486 A | 12/1998 | Davis et al. | |
| 6,070,749 A | 6/2000 | Joulia | |
| 6,454,115 B1 | 9/2002 | Allasia | |

(Continued)

FOREIGN PATENT DOCUMENTS

GB    2 363 712    1/2002

(Continued)

OTHER PUBLICATIONS

CANDY7.com website printed from the Internet (one page).

(Continued)

*Primary Examiner*—Luan K. Bui
(74) *Attorney, Agent, or Firm*—Stephen B. Parker, Esq.

(57) ABSTRACT

An oral-product container is disclosed that includes: a) a plurality of breath fresheners contained therein for breath freshening purposes; and b) a mirror for visage freshening purposes.

22 Claims, 18 Drawing Sheets

Mirror: Attached or integrally formed in interior bottom and/or top.

U.S. PATENT DOCUMENTS

| | | |
|---|---|---|
| 6,612,313 B1 | 9/2003 | Fontaine |
| 6,644,488 B1 | 11/2003 | Coleman |
| 6,976,577 B2 * | 12/2005 | Devine .................. 206/37 |
| 2002/0139802 A1 * | 10/2002 | Cross .................. 206/38 |
| 2002/0179485 A1 | 12/2002 | Shih |
| 2003/0234204 A1 | 12/2003 | Lam et al. |
| 2004/0069671 A1 | 4/2004 | Lam et al. |
| 2005/0006267 A1 | 1/2005 | Lam et al. |
| 2005/0069373 A1 | 3/2005 | Parikh et al. |

FOREIGN PATENT DOCUMENTS

| | | |
|---|---|---|
| GB | 2 363 712 A | 1/2002 |

OTHER PUBLICATIONS

Search Report in UK, Apr. 28, 2006.

* cited by examiner

Lid
hinge
Body

Mirror: Attached or integrally formed in interior of lid (i.e., sub-portion of container).

hinge

Opening into container (not shown) can be any
style and/or
size and/or shape:
-such as, e.g., as shown in FIGS. 1-3; and/or
-such as, e.g., another form of opening or the like.

Mirror: formed on either surface under hinged cover.
(Here: mirror is formed external to product containing Interior.)

Diagram A: mirror attached to container wall (e.g., mirror sticker, glue attachment, magnetic attachment and/or other).

Diagram B: mirror integral with container wall (e.g., buffed reflective surface and/or other).

Here: cover includes downward flanges that can slide around and engage the base under the peripheral lip shown.

MIRRORED ORAL-PRODUCT CONTAINER

The present application claims priority to U.S. provisional application Ser. No. 60/511,298 filed on Oct. 16, 2003, the entire disclosure of which is incorporated herein by reference as though recited herein in full.

BACKGROUND

1. Field of the Invention

The present invention relates to containers for oral-products and some preferred embodiments relate to containers for breath fresheners, such as, e.g., mints or the like.

2. Discussion of the Background

In some circumstances in modern culture, individuals seek to enhance their personal image, such as, e.g., their appearance, their odor, and/or the like. Individuals may seek to enhance their personal image for a variety of reasons, such as, by way of example, to: a) prepare for a date and/or a romantic encounter; b) make a good impression on one or more individual; c) enhance one's self-confidence; and/or d) achieve a wide variety of other goals.

Breath Freshening

In modern culture, the use of breath fresheners to, e.g., enhance an individual's oral freshness, such as, e.g., oral cleanliness, oral odor and/or the like, has become widely accepted. A wide variety of breath fresheners exist in the market, such as, e.g., various breath freshening confectionaries and candies and/or the like, such as, e.g., mint-flavored breath fresheners, cinnamon-flavored breath fresheners, fruit-flavored (such as, e.g., lemon, lime, orange and/or the like) breath fresheners; and/or the like. Some existing breath fresheners include that of, e.g., ALTOIDS, TIC TAC, BARKLEYS and various other breath freshener products.

Visage Freshening

In modern culture, the use of items to enhance an individual's visage or face is not as widely accepted. In some instances, individuals may carry compacts (having small mirrors and make-up) with which they may attend to their personal visage freshening (such as, e.g., farding).

However, while individuals often freely take breath fresheners in the accompaniment of others, individuals are often more reluctant to use a compact in the accompaniment of others. Among other things, the use of cosmetics, make-up and/or the like visage freshening products can often have a negative connotation, such as, e.g., creating an appearance of vanity. As a result, in order to be able to look at oneself in a mirror (such as, e.g., to ascertain if a need exists for visage freshening and/or to engage in visage freshening), an individual often has to leave a room to a location of privacy, such as, e.g., a bathroom or the like. While individuals may carry compacts or the like, in many contexts, individuals will not use them in the accompaniment of others. By way of example, while in a romantic setting, a woman may be reluctant to check her facial make-up in front of her partner. Among other things, the woman may not wish to portray vanity and/or to provide an appearance to her partner that she has some concern for the freshness of her visage—e.g. which might inadvertently be suggestive of personal of vanity, of a level of interest in her partner, and/or the like.

There has been a need for a product that can overcome some of the above and/or other problems.

SUMMARY OF THE INVENTION

The preferred embodiments of the present invention have been developed in view of the above mentioned and/or other issues in the related art. In some embodiments, one or more of the above and/or other problems related to visage freshening can be overcome. In addition, some preferred embodiments can advantageously provide a highly unique breath freshening container product having unique functional and aesthetic qualities.

According to some illustrative embodiments, an oral-product container includes: a) a plurality of breath fresheners contained therein for breath freshening purposes; and b) a mirror for visage freshening purposes. In some embodiments, the mirror can be on an interior of said container when said container is closed. In some embodiments, the mirror can be on an exterior of said container when said container is closed. In some illustrative embodiments, said breath fresheners include at least flavor from the group consisting of: peppermint; spearmint; other mint flavors; wintergreen; cinnamon; licorice; citric flavors; sour flavors; and herbal or spice flavors.

According to some illustrative embodiments, a method of distributing the containers can include, e.g.: filling a plurality of said containers in a packaging container; and transporting the filled packaging container to a retail center (such as, e.g., for direct sales to consumers).

According to some illustrative embodiments, a method of freshening an individual includes: providing the individual with a container having a plurality of breath fresheners contained therein and a mirror; having the individual place at least one of said breath fresheners in the individual's mouth for breath freshening purposes; and having the individual view himself or herself in said mirror for visage freshening purposes. In some embodiments, said visage freshening purposes can include determining whether the individual's face needs freshening and/or can include freshening the individual's face with cosmetic products or devices.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/ or advantages of particular embodiments should not be construed as limiting other embodiments or the claims.

BRIEF DESCRIPTION OF THE DRAWINGS

The accompanying figures are provided by way of example, without limiting the broad scope of the invention or various other embodiments, wherein:

FIGS. 10-18 are other views of containers according to some illustrative embodiments;

In particular, FIG. 10 is a front perspective view according to some embodiments, FIG. 11 is a first end view taken from the left side of the embodiment shown in FIG. 10, FIG. 12 is a second end view taken from the right side of the embodiment shown in FIG. 10, FIG. 13 is a side view taken from a front side of the embodiment shown in FIG. 10, FIG. 14 is a side view taken from a back side of the embodiment shown in FIG, FIG. 15 is a top view of the embodiment shown in FIG. 10, and FIG. 16 is a bottom view of the embodiment shown in FIG. 10;

In addition, FIG. 18 is an exploded view showing a device similar to that shown in FIG. 10 with an internal cover plate member removed and with an illustrative slider cover.

DETAILED DESCRIPTION OF THE PREFERRED EMBODIMENTS

The following description sets forth some illustrative preferred embodiments of the invention. It should be understood based on this disclosure that the following description is illustrative and non-limiting and that various modifications, alterations, changes and/or the like can be employed in various embodiments of the invention. In addition, various components of the various embodiments can be replaced with equivalent structures (including presently know equivalents and/or future known equivalents) as would be understood based on this disclosure.

Illustrative Embodiments

FIGS. 1-9 show some illustrative embodiments of the invention. In the preferred embodiments (such as, e.g., in preferred implementations of the embodiments shown in FIGS. 1-9), an oral-product container is provided that includes: a) a plurality of breath fresheners contained therein for breath freshening purposes; and b) a mirror for visage freshening purposes. Although a variety of illustrative embodiments are shown, it should be understood based on this disclosure that the illustrative embodiments can vary widely and that these are merely some preferred examples.

In preferred embodiments, the container can be used by an individual in order to orally consume one or more breath freshener for breath freshening purposes and/or to visually view himself or herself for visage freshening purposes. In this disclosure, the terminology visage freshening purposes includes, among other things, viewing for purposes of determining if a need exists for visage freshening and conducting visage freshening, such as, e.g., using cosmetic products or devices (such as, e.g., applying blush with a blush applicator, applying mascara with a mascara applicator, applying lipstick with a lipstick applicator, removing cosmetics with a cosmetic remover [which can include, e.g., a tissue and/or the like], etc.).

Figure 1:
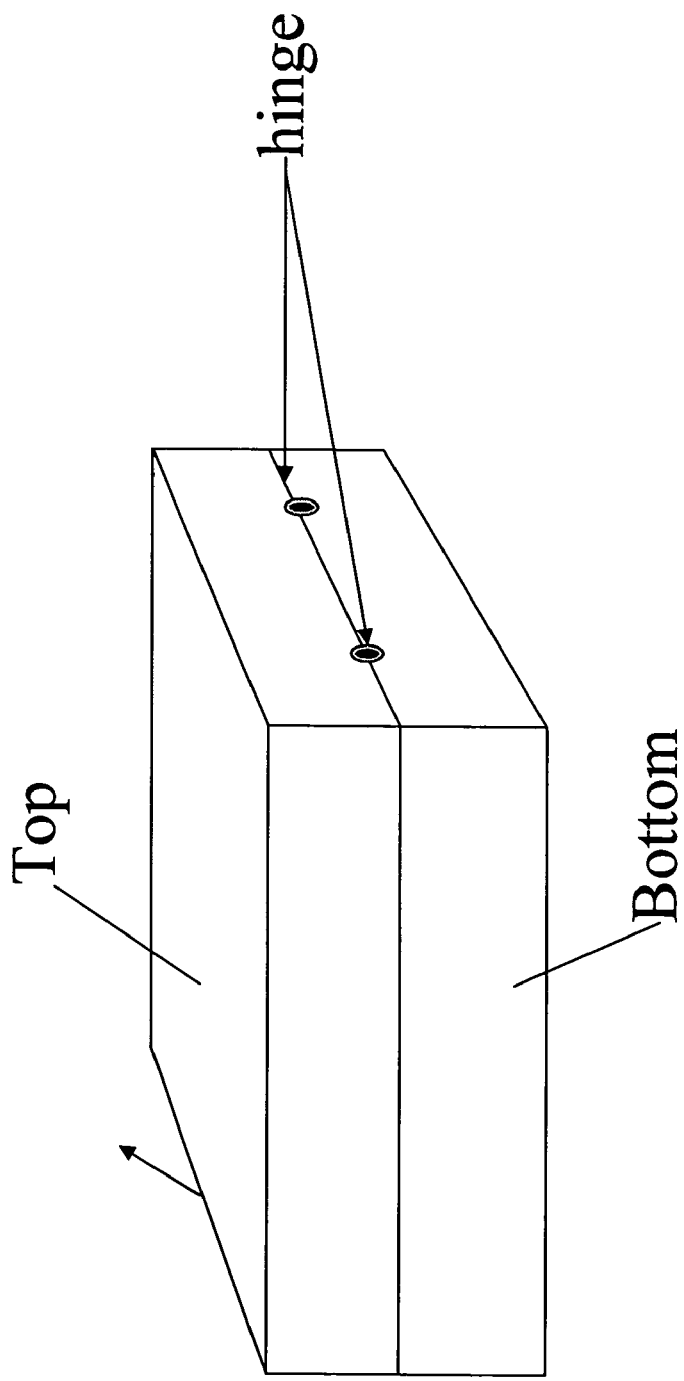
FIG. 1 is a schematic side perspective view of a container according to some illustrative embodiments.

FIG. 1 shows one illustrative embodiment including a container having top and bottom halves that are connected together via a hinge. When in a closed condition, such as, e.g., shown in FIG. 1, the two halves form an enclosure in which oral products can be contained.

In some preferred embodiments, a mirror can be formed on an interior surface of the top half. Upon pivoting the top half away from the bottom half, the mirror can be revealed. In this manner, the mirror can be—to some degree—hidden from view of those accompanying the user. Thus, a user can, e.g., take a quick look at himself or herself while appearing to merely open a container to merely access, e.g., some breath fresheners.

In some preferred embodiments, a mirror can alternatively or additionally be formed on an exterior surface of the top half. In this manner, a user can, among other things, easily utilize the mirror without regard to oral product inside the container (e.g., the user can easily utilize the mirror while the oral product is securely contained in the container).

In some preferred embodiments, a mirror can alternatively or additionally be formed on interior and/or exterior surfaces of the bottom half. Additionally, while in preferred embodiments a mirror will be formed upon a larger side of the container, in some embodiments a mirror could alternatively or additionally be formed on a narrower edge of the container (e.g., either interior and/or exterior to the container, but preferably exterior to the container).

Figure 2:
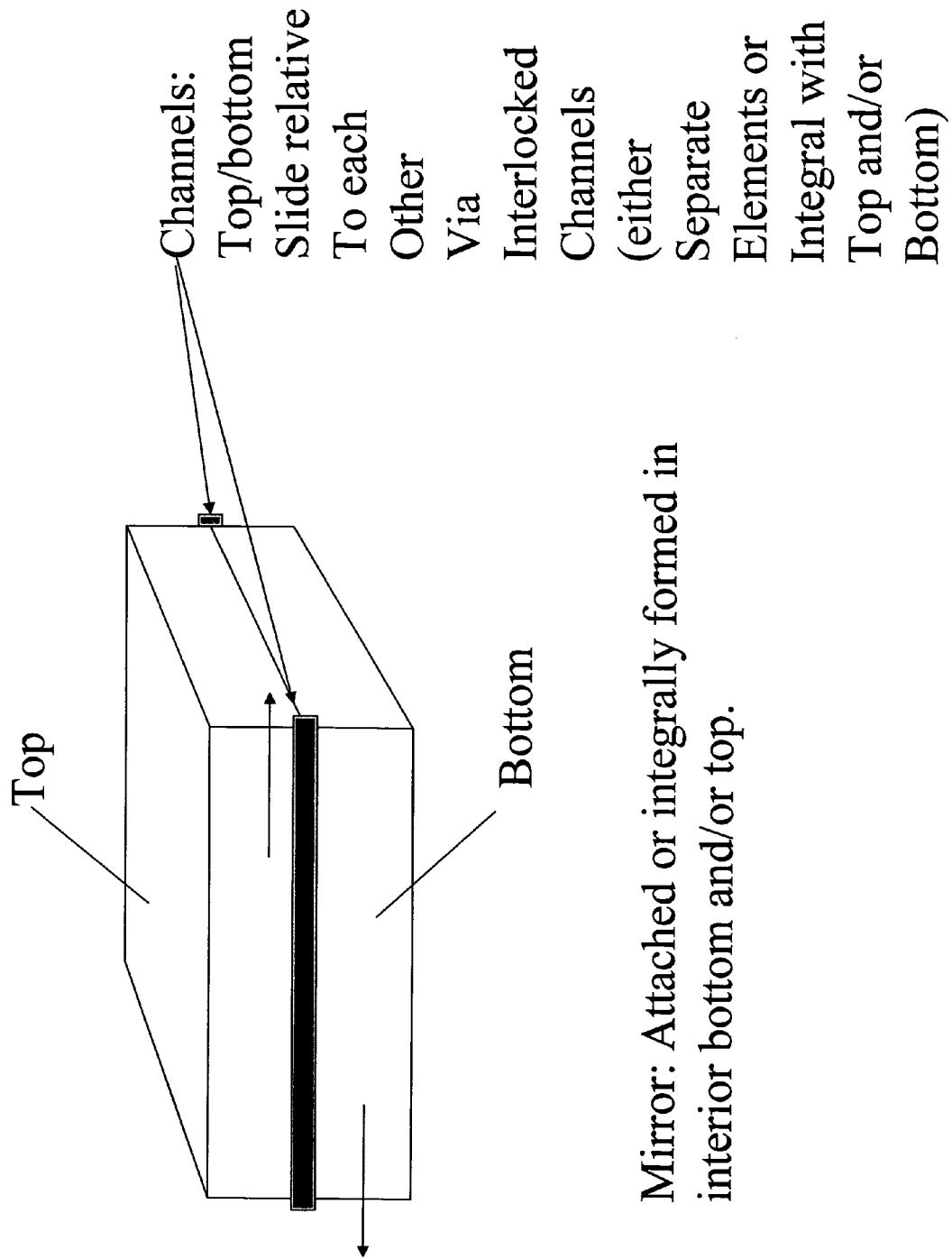
FIG. 2 is a schematic side perspective view of another container according to some illustrative embodiments.

FIG. 2 illustrates another embodiment in which a container has a top portion and a bottom portion that are laterally slidable with respect to one another in order to open the container. In this embodiment, a mirror can be formed—as before—on interior and/or exterior surfaces of the top and/or bottom portions, and upon large sides and/or narrow edges thereof.

Figure 3:
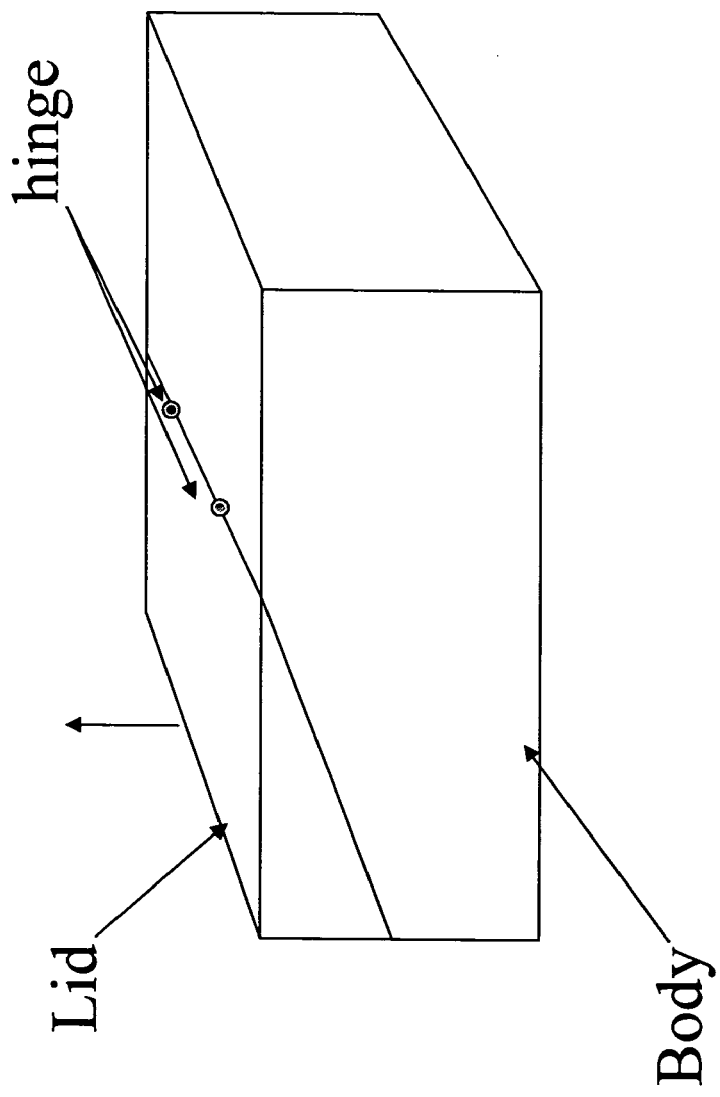
FIG. 3 is a schematic side perspective view of another container according to some illustrative embodiments.

FIG. 3 illustrates another embodiment in which a hinged lid is formed in a sub-portion of the container. Among other things, this embodiment can, e.g., facilitate opening of the container to reveal and internal mirror while the oral product is securely contained therein. In preferred implementations of this embodiment, the mirror could be formed internal to the hinged lid. However, in other embodiments, a mirror could be formed alternatively or additionally on other portions of the container.

Figure 4:
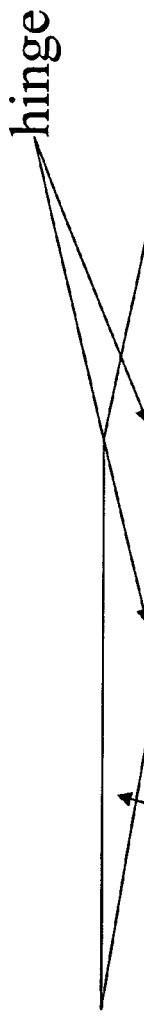
FIG. 4 is a schematic side perspective view of another container according to some illustrative embodiments.

FIG. 4 illustrates another embodiment in which a mirror can be formed underneath a separate mirror cover. In some embodiments, such as, e.g., shown in FIG. 4, the separate mirror cover can be hinged to the container. In such embodiments, a mirror can be formed on either surface under the hinged cover. In this illustrative embodiment, the mirror can be protected from external environmental factors (e.g., under the cover) and can be isolated from the container interior (e.g., separate from the oral product therein).

Figure 5:
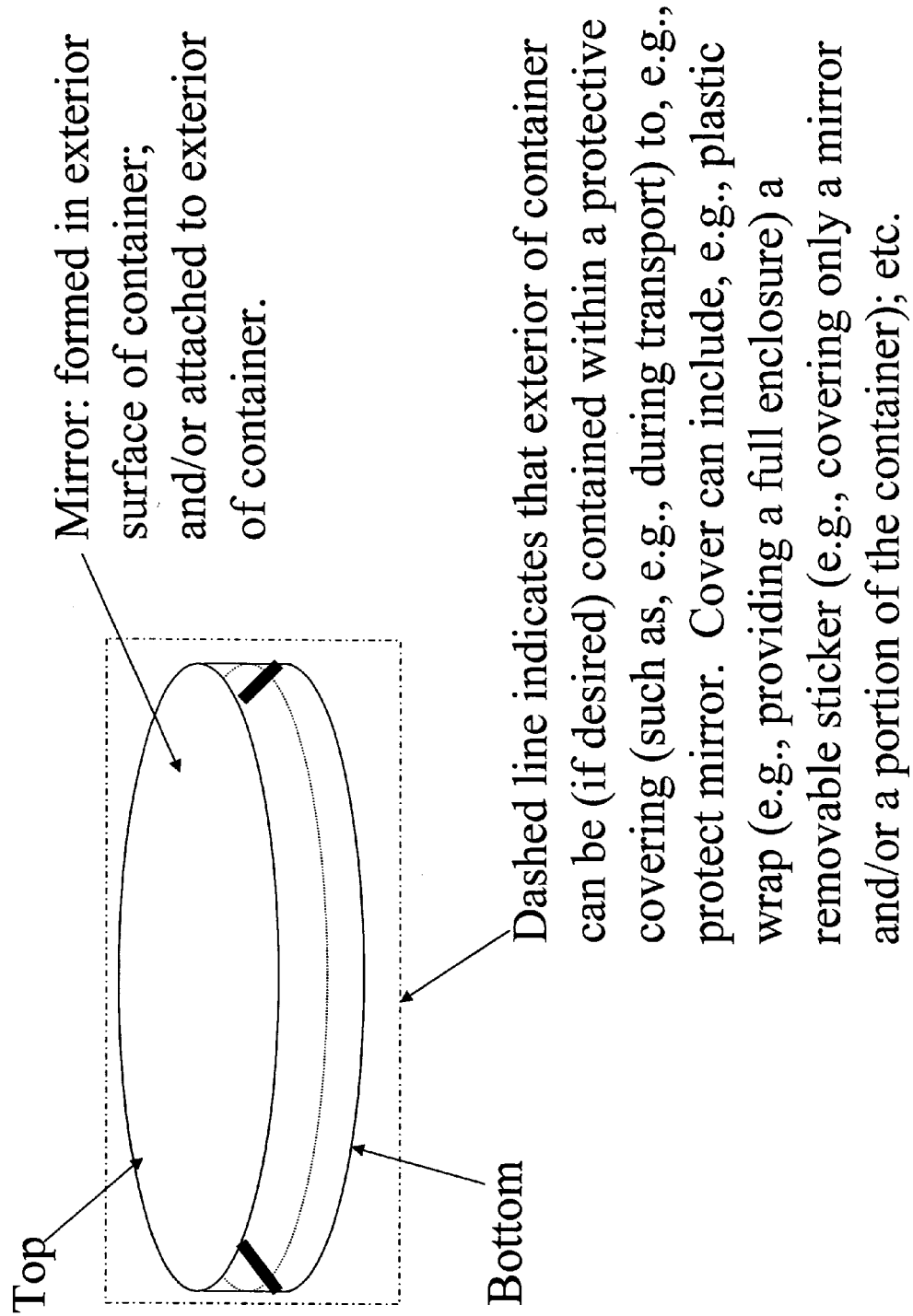
FIG. 5 is a schematic side perspective view of another container according to some illustrative embodiments.
Figure 8:
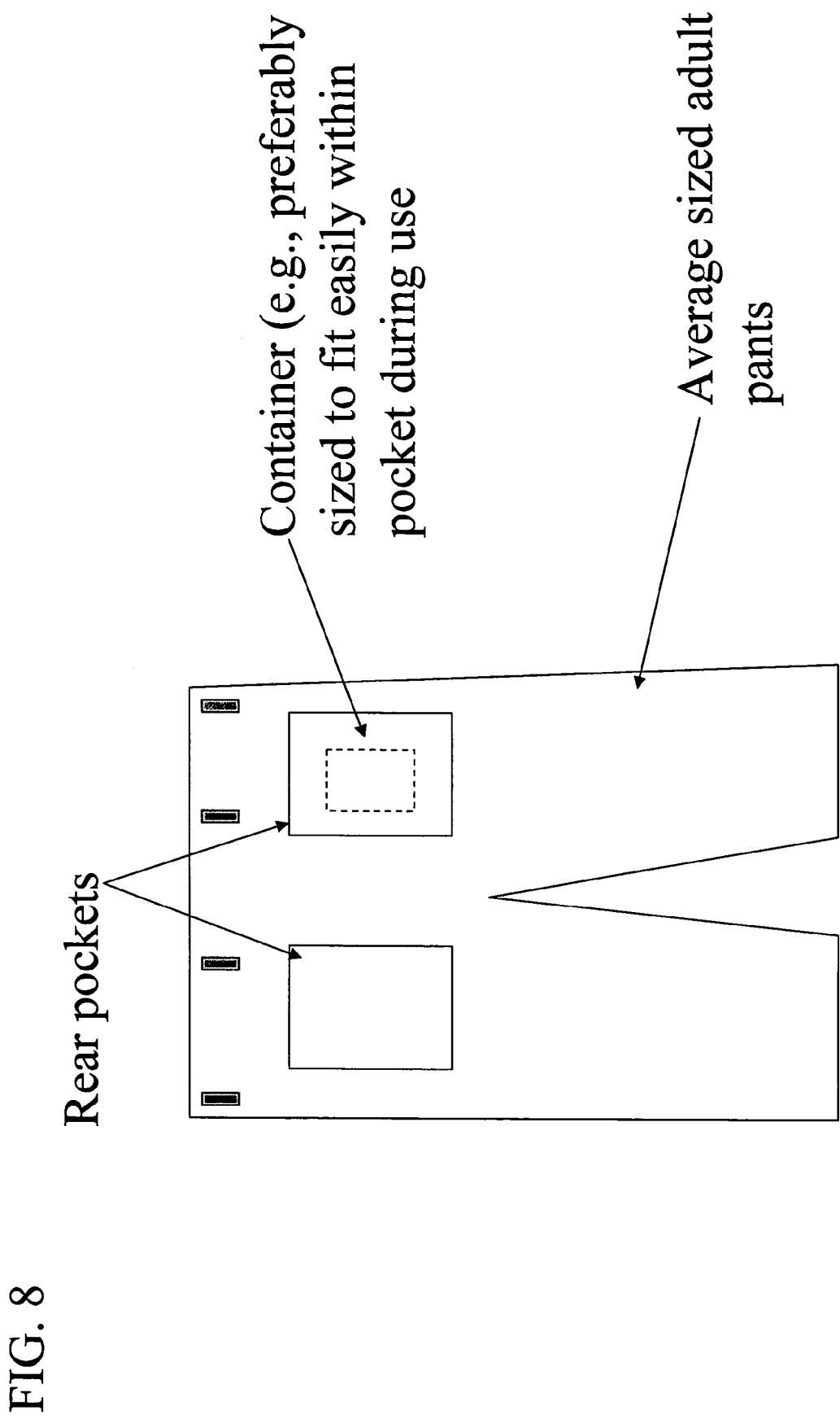
FIG. 8 is a schematic diagram showing a container located within the pants pocket of a user.

FIG. 5 illustrates another embodiment in which a container can have a generally round large side (such as, e.g., a generally circular, elliptical or other rounded shape). It should be understood that a variety of container shapes could be used and the illustrative embodiments are merely exemplary. In the most preferred embodiments, however, the container has a large side and a narrow edge. In this manner, as shown in FIG. 8, the container can, most preferably, easily slide into a storing position, such as, e.g., inside a user's pocket (such as, e.g., a rear pants pocket as shown by way of example).

In some illustrative embodiments, a large side of the container can have a maximum diameter of between about 1 inches and 6 inches. In some other illustrative embodiments, a large side of the container can have a maximum diameter of between about 2 and 5 inches. In some other illustrative embodiments, a large side of the container can have a maximum diameter of between about 3 and 4 inches. In some illustrative embodiments, a narrow side of the container can have a maximum width of between about ¼ inch and 1 inch. In some other illustrative embodiments, the narrow side of the container can have a maximum width of between about ⅓ inch and ⅔ inch. Although not shown, in some embodiments, one or more of the large sides of the container can also include a bowed configuration or curvature so as to conform to a user's buttocks when placed within a pant pocket as shown in FIG. 8.

The illustrative example shown in FIG. 5 also includes a reflective surface or mirror formed exterior to the container. It should be understood based on this disclosure that a mirror could be alternatively or additionally formed interior to the container.

Figure 6:
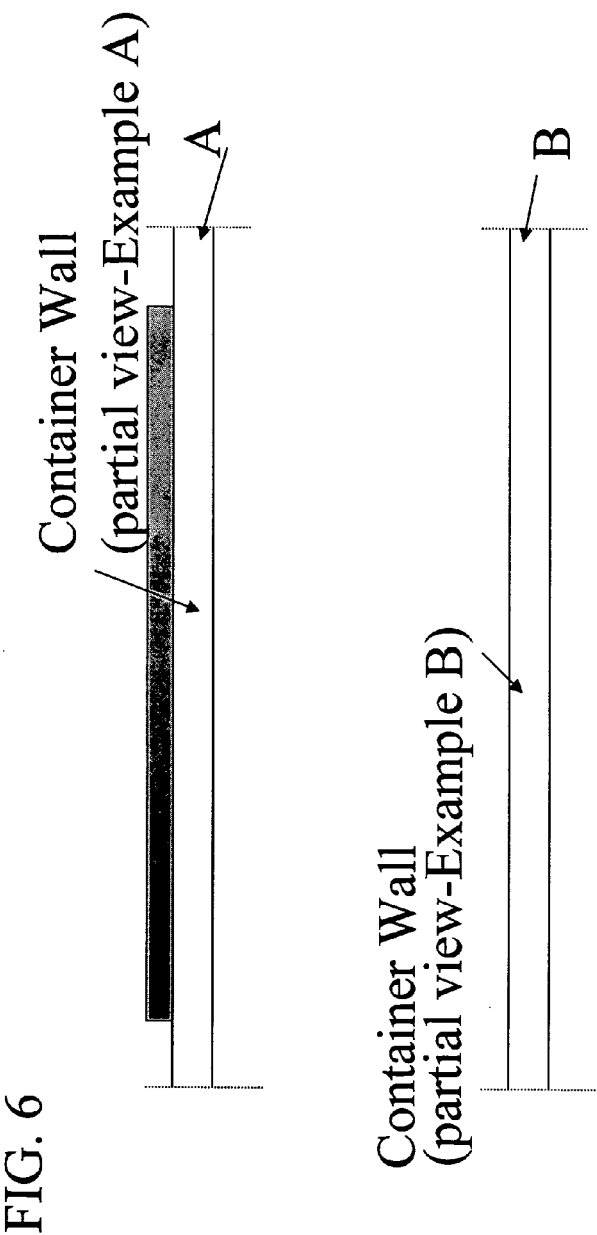
FIG. 6 is a schematic side view showing portions of illustrative examples A and B depicting some illustrative mirror forming embodiments.

FIG. 6 shows some illustrative methods for forming the mirror on the container. Example A illustrates some instances in which the mirror includes materials attached to the container wall (such as, e.g., using a mirror sticker that is applied, using glues or adhesives to attach mirror components, using a magnetic attachment, using a mechanical attachment [such as, e.g., a rivet, a screw and/or other mechanism] and/or the like). Example B illustrates some instances in which the mirror is formed integrally in the container wall (such as, e.g., a highly buffed metal surface, a chemically treated surface and/or the like).

Figure 7:
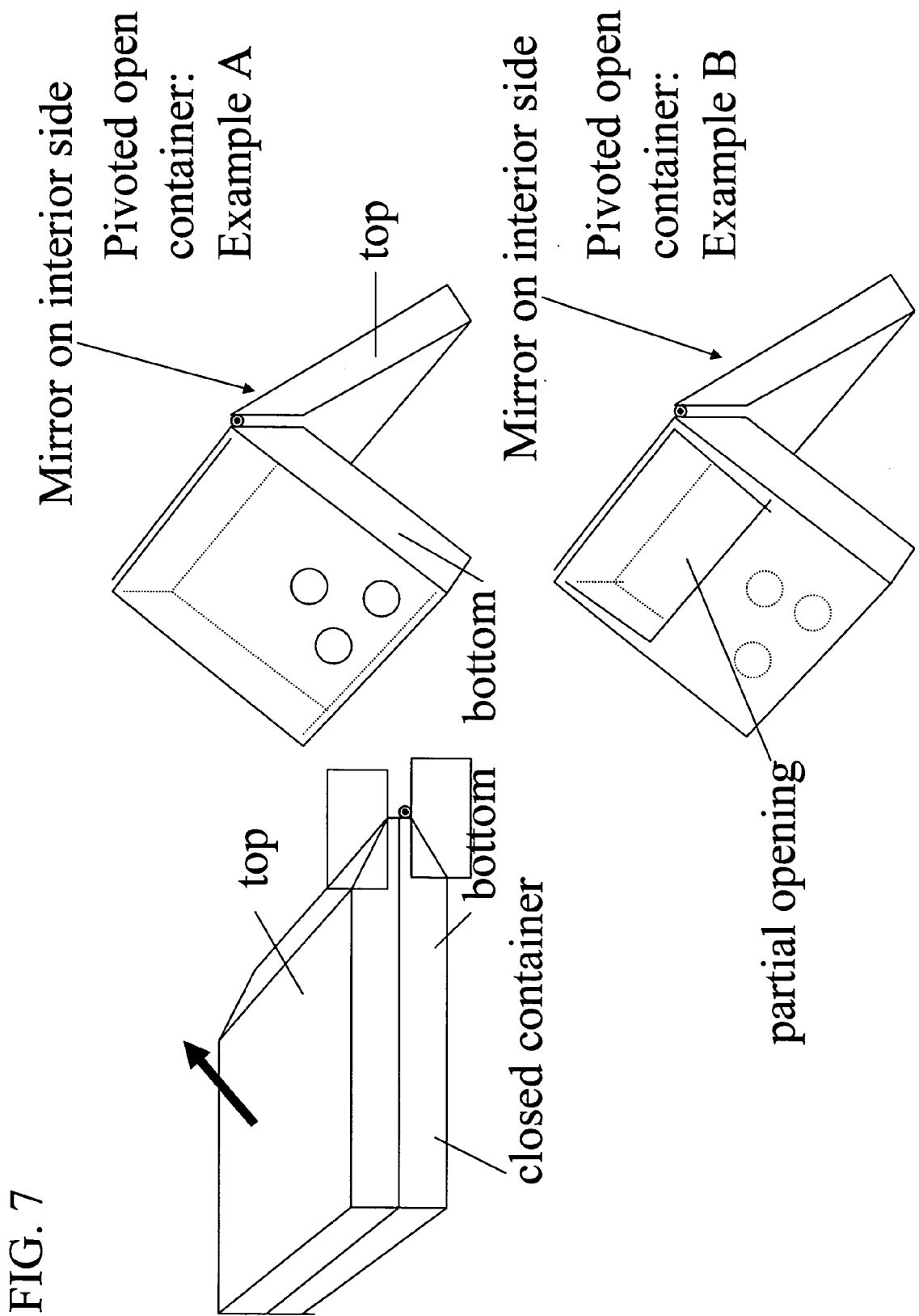
FIG. 7 is a plurality of schematic side perspective views showing other containers according to some illustrative embodiments in which the container can be operable as a mirror stand.

FIG. 7 shows some illustrative embodiments in which a container has an open position in which the container serves as a stand for the mirror. While the container can serve as a stand for the mirror using a variety of other configurations (as would be apparent based on this disclosure), in the illustrative embodiment, the container can include an internal mirror on a top half of the container. The container can then be configured such that when it is pivoted open, it can be placed in a fully open position as shown in FIG. 7 in which the container forms a generally A-frame structure or a generally inverted-V structure as shown. Preferably, the container is configured such that the container is lockable in an open position and/or in a closed position (such as, e.g., providing snap-fit engaging members between the top and bottom portions).

FIG. 7 also shows two illustrative examples: Example A shows an opened container having a substantially fully open bottom; and Example B shows an opened container having a partially open bottom. Among other things, Example B can facilitate use of the container in the open position while breath fresheners (shown in dashed lines in Example B) are securely retained in the container.

In some preferred embodiments, the container can be made with metal, such as, e.g., of tin, aluminum, stainless steel, iron, copper and/or other metal. In some preferred embodiments, the container can be made with natural and/or synthetic resins, such as, e.g., various plastics and/or the like. In some preferred embodiments, the container can be made with paper, cardboard, wood and/or the like materials. In some preferred embodiments, the container can be shrouded within a plastic wrap and/or another wrapping medium, such as, e.g., a foil wrap. Among other things, such a wrap can help to protect the contents within the container and/or can help to protect the container itself. Such a plastic wrap could be, e.g., a manually removable wrap that is removed by an end consumer who uses the container for oral and/or visage freshening purposes. In some embodiments, a plurality of containers can be wrapped together for bulk sales to a consumer (such as, e.g., in groups of 2, 4, 6, 12 and/or the like).

Mirror(s)

In various embodiments, a number of mirror constructions can be employed. For example, in some embodiments one or more of the following types of mirrors (i.e., reflective surfaces) can be employed.

1. A glass with a reflective coating (such as, e.g., a metal undercoating), such as, e.g., a common household mirror;
2. A polymer material with a reflective coating;
3. A metal, such as, e.g., aluminum, chrome and/or other metal having a highly reflective surface (such as, e.g., a buffed surface and/or otherwise smooth and reflective surface finish and/or the like).

In preferred embodiments, the mirror has a sufficient extent of reflectivity to enable an individual to hold the mirror or otherwise locate the mirror within about 6 inches to 1 foot, or even within about 1 foot to 2 feet, from the individual's face and to visually perceive facial details without significant content distortion. In preferred embodiments, the reflectivity is sufficient to enable a user to perform common cosmetic visage freshening tasks.

In some preferred embodiments, the mirrors are made with one or more of the following properties: a) breakproof or substantially breakproof materials; b) shatterproof or substantial shatterproof materials; c) appropriate non-toxic materials for food product packaging; and/or d) other appropriate properties for food product packaging.

In some illustrative embodiments, mirrors can employ aspects of one or more of the features of the mirrors shown in the following documents (each of which are incorporated herein by reference in their entireties and are included in the above-reference provisional application):

1. http://www.ultralight-sports.com/mirror.html (including, e.g., mirrors made from made from a premium reflective plastic film laminated to smooth coated paper);
2. http://www.e-sci.com/genSci/RENDER/7/1035/1080/9982.html (including, e.g., mirrors having a substrate that is acrylic with an aluminum coating for a reflecting surface);
3. http://www.goodturn.biz/mirrors.html
4. http://www.csmirrors.co.uk/index.php?pageID=acrylic (including, e.g., acrylic mirrors);
5. http://www.csmirrors.co.uk/index.php?pageID=stainlesssteel (including, e.g., stainless steel mirrors);
6. http://www.alsacorp.com/Laminates.html (including, e.g., "ChromeFX sheeting [that] is a decorative product based upon GE HP92H LEXAN® films and a Molecular Metallic Chrome Film protected by the LEXAN® film and backed by an adhesive system").

Oral Products

In various embodiments, a plethora of different oral-products can be contained within the containers. In some embodiments, the oral-products can include, e.g., breath fresheners. For example, such breath fresheners may, e.g., enhance an individual's oral freshness, such as, e.g., oral cleanliness, oral odor and/or the like. Various embodiments can use any currently known and/or later known fresheners, such as, e.g., various breath freshening candies and/or the like, such as, e.g., mint-flavored fresheners, cinnamon-flavored fresheners, fruit-flavored (such as, e.g., lemon, lime, orange and/or the like) fresheners and/or the like. In some embodiments, breath fresheners similar to, e.g., ALTOIDS, TIC TACS, BARKLEYS, CERTS and/or various other breath freshener products can be used.

In some illustrative embodiments, oral products can include one or more of the following:
  a) gum (such as, e.g., wrapped chewing gum strips [such as, e.g., WRIGLEY'S BIG RED gum sticks, WRIGLEY'S SPEARMINT gum sticks, etc.], gum balls [such as, e.g., EVERCREST mint gum balls, etc.]);
  b) candy coated gum (such as, e.g., WRIGLEY'S ECLIPSE rectangular gum chews);
  c) hard-confectionary (such as, e.g., hard mints);
  d) quick-dissolving confectionary (such as, e.g., quick dissolving mints)(such as, e.g., lasting under about 30 seconds in normal usage in an adult user's mouth);
  e) slow-dissolving confectionary (such as, e.g., longer lasting mints or lozenges)(such as, e.g., lasting over one minute in normal usage in an adult user's mouth); and/or
  f) strip-shaped confectionary (such as, e.g., ALTOIDS strips and/or LISTERINE POCKET PACKS, etc.).

While a variety of illustrative oral products are described herein, it should be understood based on this disclosure that various embodiments can employ a variety of other oral products (such as, e.g., various food products [e.g., candies, confectioneries or other food products], medicinal products, flavored products and/or the like).

In some embodiments, the oral products can include breath fresheners having one or more of the following flavors: peppermint, spearmint; other mint flavors; wintergreen; cinnamon; licorice; citric flavors (e.g., lemon, orange, lime, etc.); sour flavors; herbal or spice flavors (e.g., garlic, onion and/or the like) and/or other now or later known breath freshener flavors.

In some embodiments, the oral products include all or substantially all natural ingredients. In some embodiments, all or substantially all of the ingredients contributing to the flavor of the oral products are natural ingredients.

In some embodiments, the oral products can include at least some or all of the following ingredients (such as, e.g., found in BARKLEYS PEPPERMINT mints): sugar; powdered glucose; sorbitol; maltodextrin; magnesium stearate; oil of peppermint (e.g., triple distilled oil of peppermint); natural and artificial flavors. In some embodiments, the oral products can include at least some or all of the following ingredients (such as, e.g., found in BARKLEYS WINTERGREEN mints): sugar; powdered glucose; maltodextrin; magnesium stearate; artificial flavors. In some embodiments, the oral products can include at least some or all of the following ingredients (such as, e.g., found in BARKLEYS CINNAMON mints): sugar; powdered glucose; maltodextrin; magnesium stearate; natural and artificial flavors; oil of peppermint.

In some embodiments, the oral products have very low calories. In some embodiments, the oral products have very low carbohydrate values, such as, e.g., less than about 10 grams per serving, or, more preferably, less than about 5 grams per serving, or, more preferably, less than about 3 grams per serving, or, more preferably, less than about 2 grams per serving.

In some embodiments, one or more of the following ingredients can be used to create a breath freshener product: sugar, dextrin, starch, arabic gum, natural and artificial flavors, magnesium stearate, carnauba wax (such as, e.g., found in TIC TACS). In some embodiments, there will not be a significant source of calories from fat, saturated fat, cholesterol, fiber, vitamin A, vitamin C, calcium and/or iron.

In some illustrative embodiments, the breath fresheners can have a serving size of 1 piece (such as, e.g., about 0.3-0.4 grams per piece), can come in containers having about 30-50 per container, and can have a total amount of calories per serving of about 1-2 calories (such as, e.g., found in TIC TACS).

In some illustrative embodiments, each piece can have one or more, preferably all, of the following amounts (followed by % of daily value): total fat: 0 g, 0%; sodium: 0 mg, 0%; total carbohydrates: 0 g, 0%; sugars, 0 g; and/or protein, 0 g.

In some embodiments, the breath fresheners can include one or more of the following ingredients (such as, e.g., found in ALTOIDS WINTERGREEN mints): sugar; artificial flavor; gum arabic; gelatin; glucose syrup; natural Flavor.

In some embodiments, the breath fresheners can include one or more of the following nutrition facts (such as, e.g., found in ALTOIDS WINTERGREEN mints): serving size=3 pieces (about 2 g); servings per container=about 50; calories total=about 10; calories from fat=about 0.

In some embodiments, the breath fresheners can include one or more of the following ingredients (such as, e.g., found in ALTOIDS PEPPERMINT): sugar; oil of peppermint, gum arabic, gelatin, corn syrup.

In some embodiments, the breath fresheners can be made to temporarily mask bad breath and/or a bad taste in one's mouth. In some embodiments, the breath fresheners can be made to (e.g. using chemicals, compounds or the like) help reduce bacteria (e.g., anaerobic bacteria) in a user's mouth.

In some embodiments, the breath fresheners can include, e.g., retsyn, partially hydrogenated cottonseed oil and/or copper gluconate.

In some embodiments, the breath fresheners can include chlorophyll (such as, e.g., in CLORETS) and/or the like to, for example, help absorb or reduce bad odors.

In some embodiments, the breath fresheners can include maltitol and/or other sweeteners.

In some embodiments, the breath fresheners can include xylitol. Among other things, xylitol can be used as a natural sweetener that may help avoid and/or fight cavities.

In some embodiments, the breath fresheners can include zinc gluconate (which, e.g., may block receptors on the anaerobic bacteria such that they will not bind with certain amino acids) such as in, e.g., ZOX mints.

In some embodiments, in which the breath fresheners include components that reduce bacteria, the breath fresheners can include one or more aspect of LISTERINE POCKET PAKS oral strips. In some embodiments, the strips can dissolve quickly in a user's mouth (such as, e.g., within about 30 seconds).

In some embodiments, the breath fresheners can include one or more of the following ingredients (such as, e.g., found in LISTERINE POCKET PAKS): pullulan; flavors; menthol; aspartame; potassium acesulfame; copper gluconate; polysorbate 80; carrageenan; glyceryl oleate; eucalyptol; methyl salicylate; thymol; locust bean gum; propylene glycol; xanthan gum; coloring (e.g., FD&C green no. 3).

In some embodiments, the breath fresheners can include one or more ingredient having anesthetic properties, such as, e.g., dyclonine and/or hexylresorcinol (which can be found in, e.g., SUCRETS lozenges) and/or other anesthetic elements.

In some examples, as set forth above, the breath fresheners can include gum breath fresheners. In some illustrative example, gum breath fresheners can include one or more of the following ingredients (such as, e.g., found in WRIGLEY'S ECLIPSE peppermint gum): maltitol; gum base; sorbitol; acacia; mannitol; glycerol; natural and artificial flavors; aspartame; color added; acesulfame K; carnauba wax; BHT (to maintain freshness); phenylalanine and/or the like. In some illustrative example, gum breath fresheners can include one or more of the following ingredients (such as, e.g., found in EVEREST POWERFUL MINT GUM: ECLIPSE peppermint gum): sugar; gum base; corn syrup; dextrose; natural flavors (including, e.g., peppermint oil); gum Arabic; xylitol and, e.g., about 2% or less of glycerine, titanium dioxide (or other colorant), confectioner's glaze, carnauba wax, acesulfame K, aspartame, maltodextrin, BHT; and/or the like. In some illustrative example, gum breath fresheners can include one or more of the following ingredients (such as, e.g., found in WRIGLEY'S SPEARMINT chewing gum sticks): sugar; gum base; corn syrup; dextrose; natural and artificial flavors, softeners, acesulfame K, BHT and/or the like).

In some embodiments, each individual breath freshener can be individually wrapped within the container (such as, e.g., gum sticks which can, e.g., be wrapped with a paper material, a plastic material, a foil material (such as, e.g., a metalized foil, etc.) and/or the like. In some embodiments, two or more sets of a plurality of breath fresheners can be separately wrapped within the container. In some embodiments, all of the breath fresheners in the container can be wrapped insider the container, such as, e.g., using a paper wrap inside of a container (such as, e.g., seen in ALTOIDS mints).

In some embodiments, when an internal mirror is employed, preferably the oral-products will not have a significant tendency to crumble such that particulate material (such as, e.g., dust from mints or the like) does not accumulate on the mirror.

Figure 9:
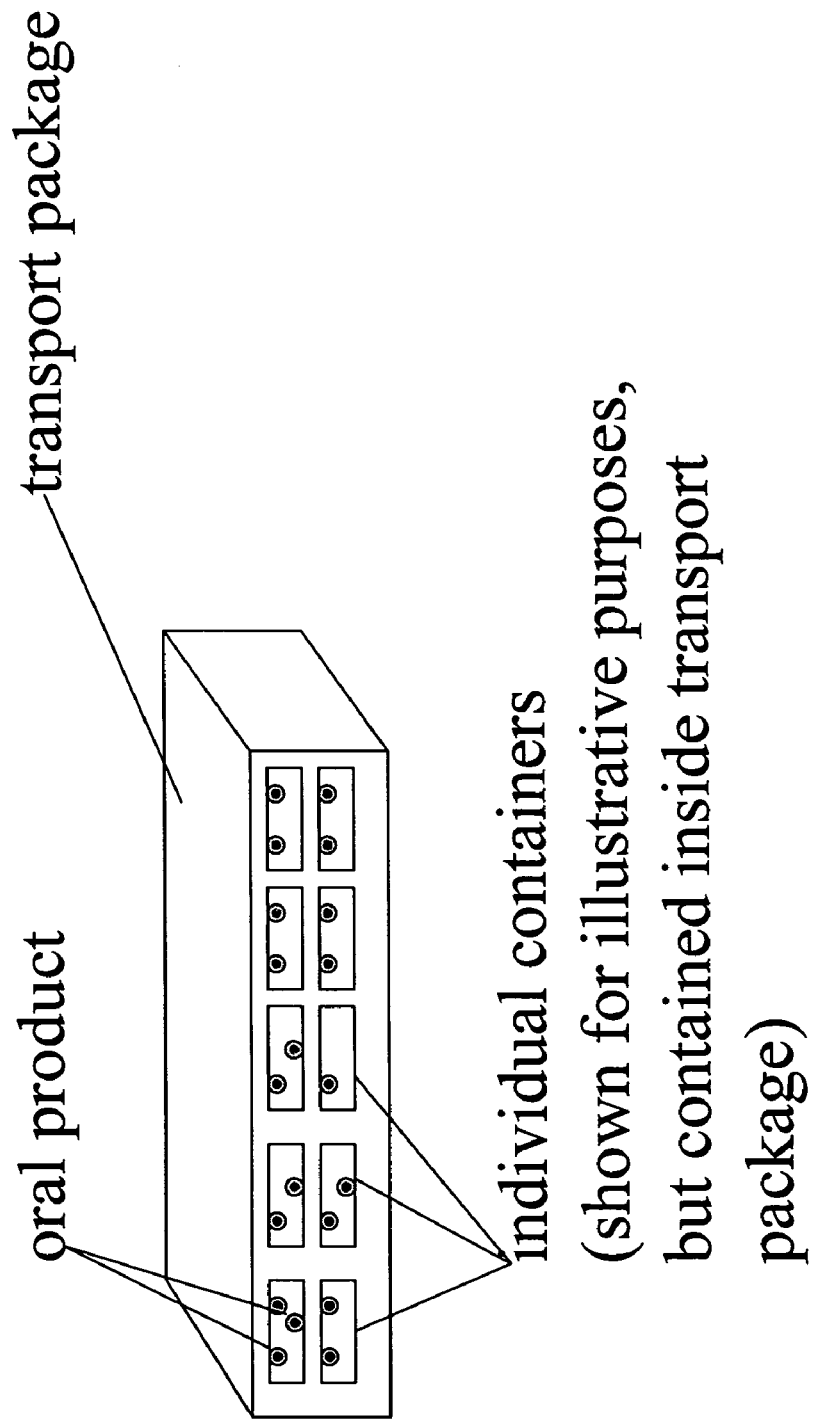
FIG. 9 is a schematic diagram showing a plurality of containers filled with oral products, such as, e.g., breath fresheners, contained within a transport package (such as, e.g., a crate, cardboard box, box and/or the like)

With reference to FIG. 9, the figure shows a schematic diagram with a plurality of containers filled with oral products, such as, e.g., breath fresheners, contained within a transport package (such as, e.g., a crate, cardboard box, box and/or the like) according to some preferred embodiments. In this regard, in some embodiments, the oral product filled containers are preferably packaged with a plurality of oral products therein by a manufacturer and/or the like. Then, the products are preferably sold and transported in a packaged state to distributors and/or retailers. Then, the products are preferably sold to end customers or users of the products. In some preferred embodiments, a multitude of filled containers are packaged in transport packages for transport from the manufacturer to the distributor(s) and/or the retailer(s) and/or for transport to the end customer(s).

As described above with reference to FIG. 4, in some embodiments a mirror can be formed underneath a separate mirror cover. In that regard, FIG. 4 shows a mirror cover that can be hinged to the container or that can include any other "covers or doors that are moved using other now or later known methodologies" (language quoted from below under Broad Scope of the Invention) such as, by way of example, employing a slider cover similar to that shown in FIG. 2. In this regard, FIG. 18 shows some illustrative embodiments in which a slidable mirror cover can be used to cover a container having a base and a mirror supporting insert fitted therein. Notably, in preferred embodiments, the base and the insert together form a structure that can be similar to that shown in FIGS. 10-17(D). As discussed above, in these types of illustrative embodiments employing a separate mirror cover, the mirror can be protected from external environmental factors (e.g., under the cover) and can be isolated from the container interior (e.g., separate from the oral product therein).

Figure 10:
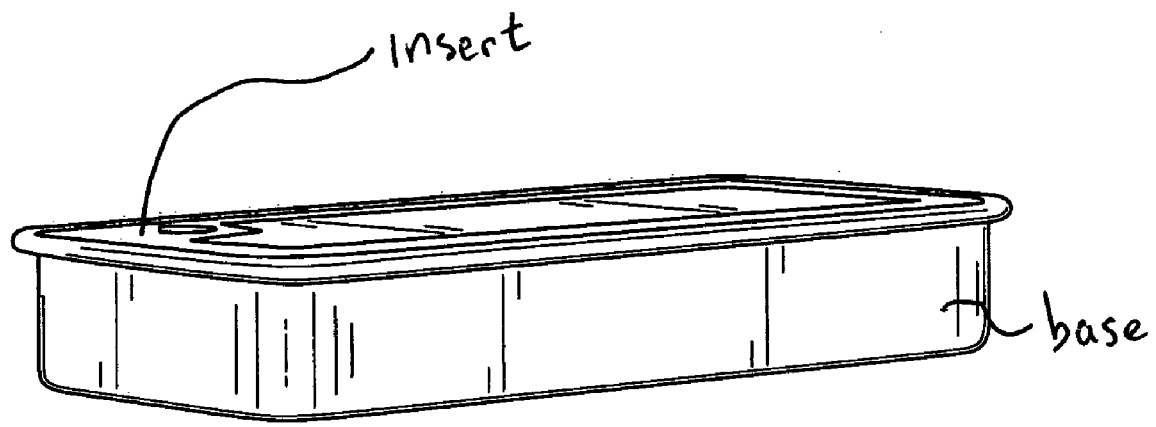
Figure 11:
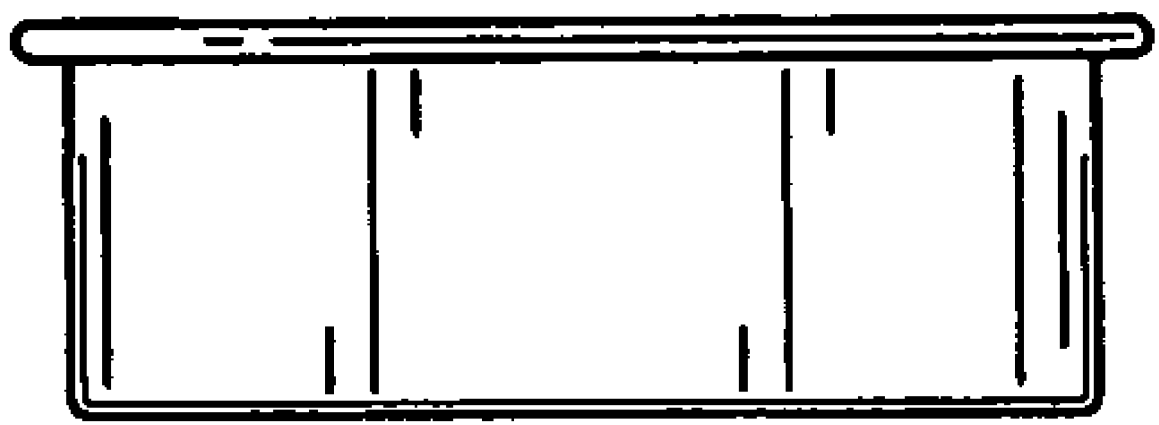
Figure 12:
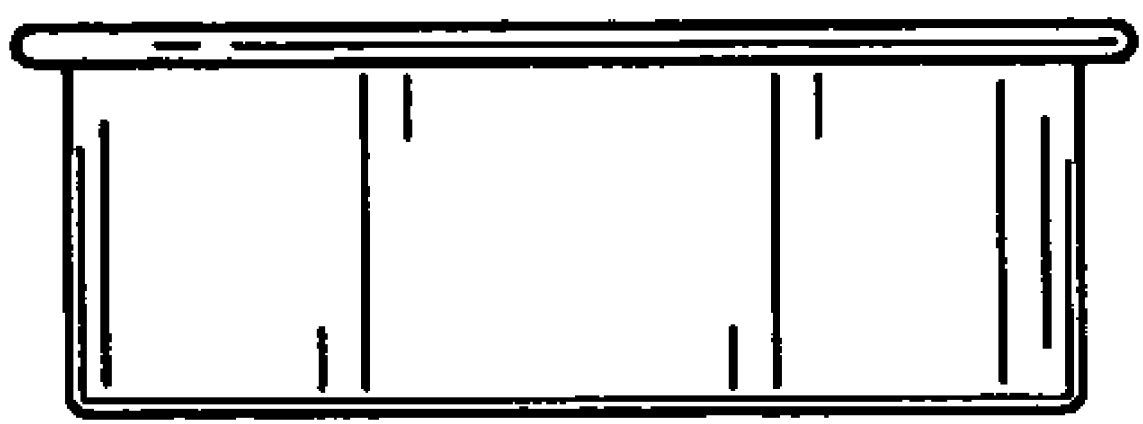
Figure 13:
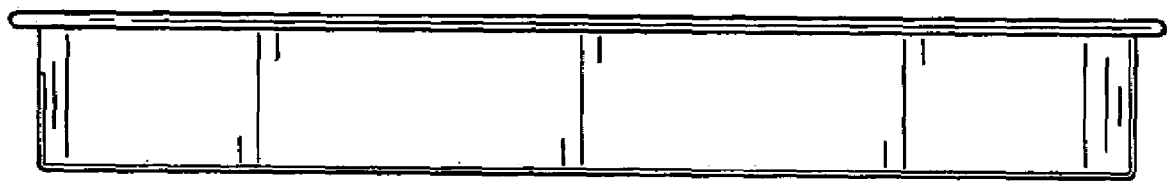
Figure 14:
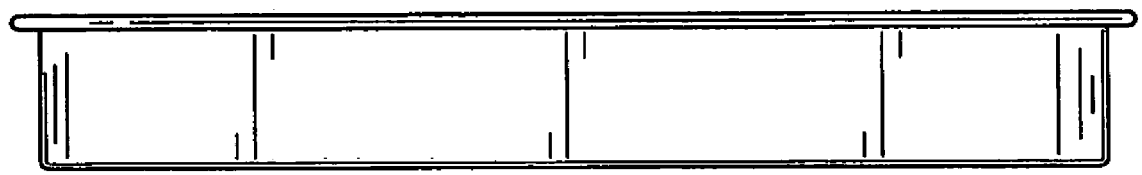
Figure 15:
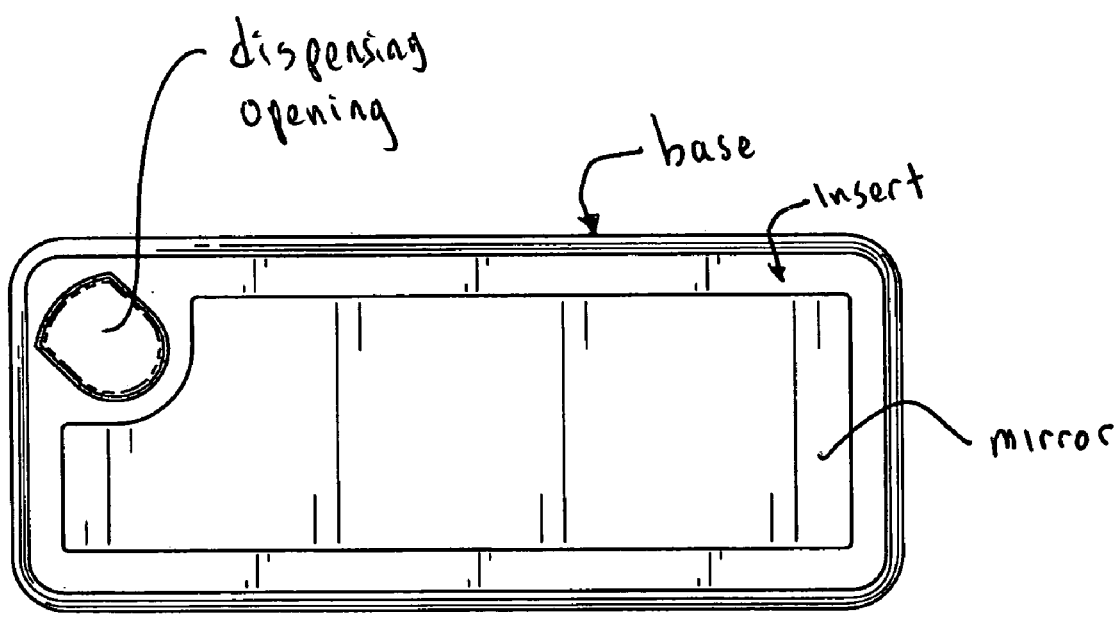
Figure 16:
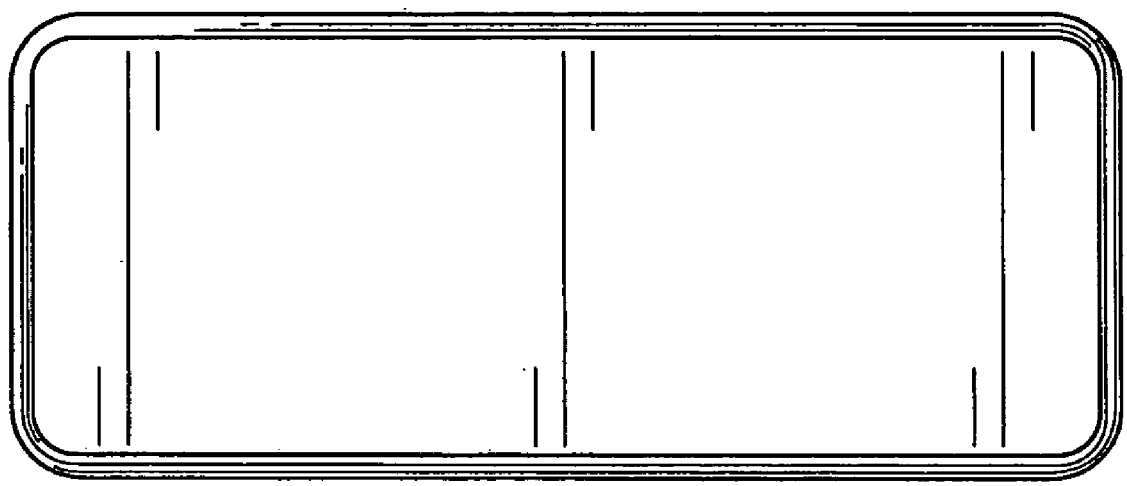

As described above, FIG. 10 is a front perspective view according to some embodiments, FIG. 11 is a first end view taken from the left side of the embodiment shown in FIG. 10, FIG. 12 is a second end view taken from the right side of the embodiment shown in FIG. 10, FIG. 13 is a side view taken from a front side of the embodiment shown in FIG. 10, FIG. 14 is a side view taken from a back side of the embodiment shown in FIG, FIG. 15 is a top view of the embodiment shown in FIG. 10, and FIG. 16 is a bottom view of the embodiment shown in FIG. 10.

In the preferred embodiments, in the device shown in FIG. 10, a base (which is preferably formed of metal, such as, e.g., aluminum, steel, tin and/or any other appropriate metal) is provided that contains (e.g., snugly receives) an insert (which is preferably formed of plastic or the like) that supports a mirror as shown. In this regard, as shown in FIG. 15, the insert preferably includes a mirror that is mounted thereon. For example, the insert can include a recess that is configured to surround the mirror and to support the mirror such that a front face of the mirror is substantially flush with a front face of the insert.

In the preferred embodiments, as shown in FIG. 18, during assembly, the insert can be initially removed. Then, product (e.g., mints can be easily loaded into the base). Then, the insert can be easily placed over the product so as to contain the same within the base. Preferably, the insert includes a plurality of depending wide leg portions that taper slightly inwards to snugly wedge into the base when inserted (in the illustrated embodiment, four leg portions are shown by way of example). Preferably, the legs slide freely around any product within the base. In this manner, filling is simplified and does not need to be done via the small dispensing opening or the like. In this manner, the mirror can be supported external to the product. In addition, the mirror can be supported internal to an external cover. In addition, the mirror can be supported on a substantially rigid, but flexibly member (e.g., using a plastic insert having some resiliency) such that if the cover does bend, the insert can have some freedom of movement further protecting the mirror in some embodiments.

With reference to FIG. 15, in some embodiments, the dispensing opening includes a punch-put cover plate (not shown) sized to fit the opening. For instance, the plate could attach a few points around the opening to the insert body. Then, upon use, a user could punch out the plate and discard the cover plate or push the same down into the container. In some embodiments, however, the opening does not need to employ a cover plate, but the small opening can remain open. In the preferred embodiments, however, the insert substantially separates the mirror from the product compartment area (with, in some embodiments, a small exception for the region of the dispensing opening if such is open).

Figure 17A:
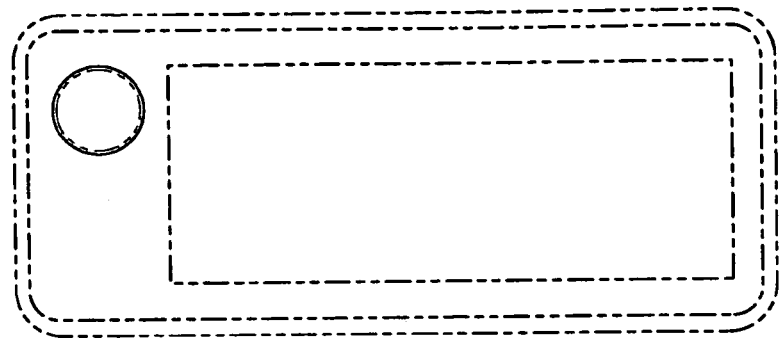
FIGS. 17(A)-17(D) show various alternative top views that may be employed instead of the structure shown in FIG. 15.
Figure 17B:
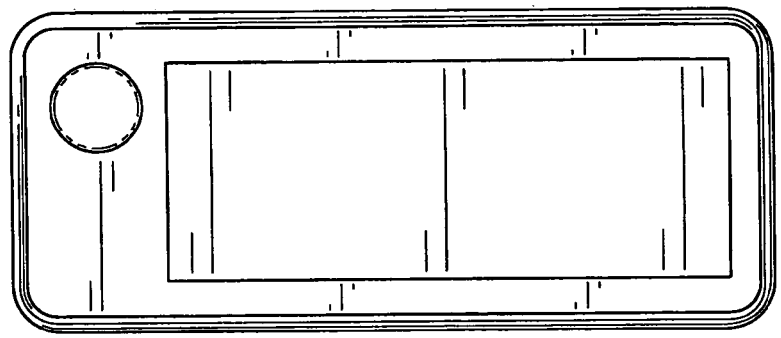
Figure 17C:
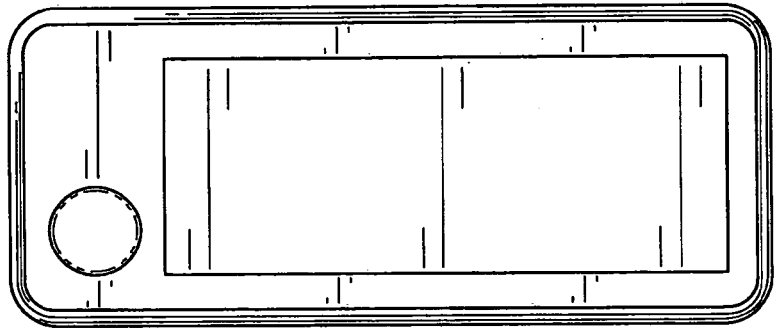
Figure 17D:
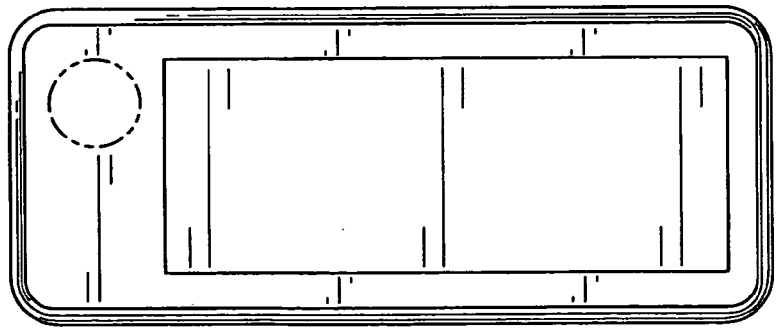
Figure 18:
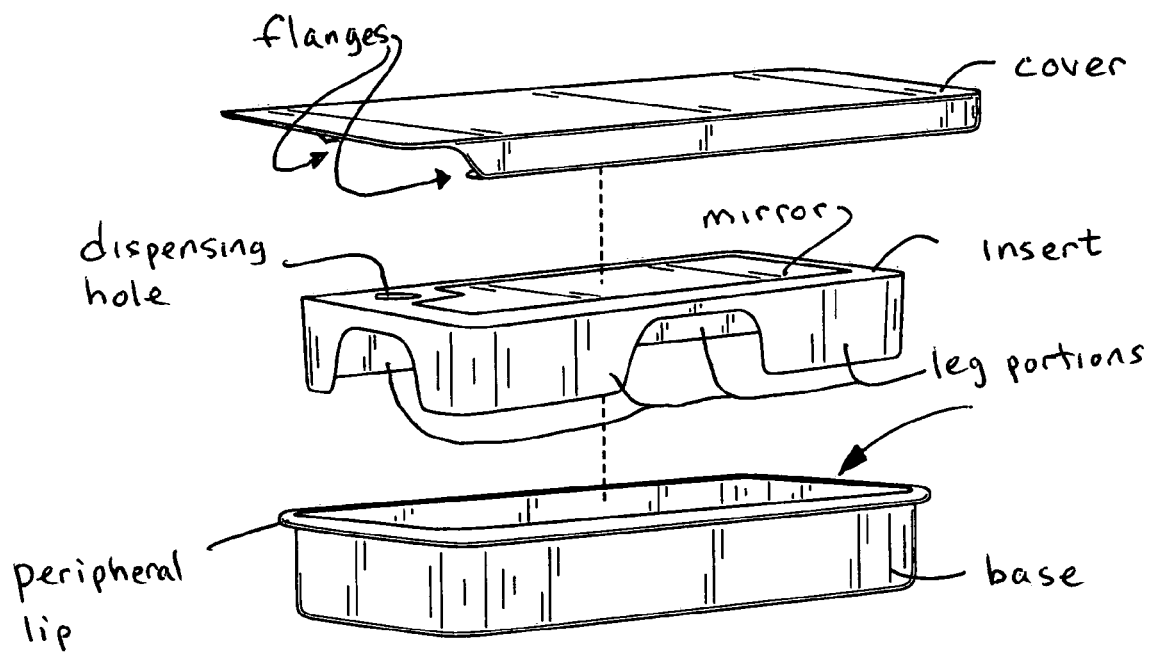

With respect to FIGS. 17(A)-17(D), these embodiments show other variations in which: FIG. 17(A) shows a view in which all lines shown in dashes are optional, but where the container includes a small opening in the upper surface at the location shown (NB: the opening can have a variety of shapes an this embodiment shows an illustrative circular opening which can be employed); FIG. 17(B) shows a view in which the mirror is not formed to surround the opening, but is formed into a generally rectangular configuration (NB: this embodiment also shows an illustrative circular opening); FIG. 17(C) is similar to FIG. 17(B) with the opening at a different location; and FIG. 17(D) is similar to the embodiments shown in FIGS. 17(B) and 17(C) but shows the opening in dashed lines to demonstrate that in other embodiments, the opening can be at any other desired location (such as, e.g., even formed into the base or another location or the like.

With respect to the embodiments shown in FIGS. 10-18, these embodiments depict some preferred embodiments, substantially to scale according to some preferred embodiments of the invention. In some preferred embodiments, devices having the ornamental design as shown in these FIGS. are preferably implemented, which figures are substantially to scale and proportional in some illustrative embodiments.

Broad Scope of the Invention

While illustrative embodiments of the invention have been described herein, the present invention is not limited to the various preferred embodiments described herein, but includes any and all embodiments having modifications, omissions, combinations (e.g., of aspects across various embodiments), adaptations and/or alterations as would be appreciated by those in the art based on the present disclosure. As merely other examples, various other embodiments can include containers with fully removable covers, replaceable covers and/or covers or doors that are moved using other now or later known methodologies. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. An oral-product container, comprising:
   a) a plurality of breath fresheners contained therein for breath freshening purposes;
   b) a mirror unmovably fixed to said container for visage freshening purposes;
   c) a mirror cover such that the mirror can be protected from external environmental factors under the cover;
   d) wherein said mirror is isolated from the container interior such as to be separate from the oral product; and
   e) wherein said mirror is suoported on a wall that is fixed relative to an opening in said container through which said breath fresheners are dispensed.

2. The oral-product container of claim 1, wherein said mirror is supported underneath said cover and wherein said cover is mounted so as to move relatively to said mirror to expose said opening.

3. The oral-product container of claim 2, wherein said cover is mounted so as to slide laterally in a plane substantially parallel to said mirror.

4. The oral-product container of claim 2, wherein said cover is mounted so as to pivot relatively to said mirror.

5. An oral-product container, comprising:
   a) a container body;
   b) a plurality of breath fresheners or candies within said container;
   b) a laterally sliding lid on said container body;
   c) a mirror beneath said laterally sliding lid and unmovably fixed to said container body;
   d) wherein said container is configured to expose both said mirror and an oral-product dispensing opening by lateral motion of said lid.

6. The oral product container of claim 5, wherein said oral-product dispensing opening is on a common wall with said mirror.

7. The oral-product container of claim 5, wherein said product dispensing opening is sized to dispense only a few breath fresheners or candies at a time and is substantially smaller than a side face of the container through which said dispensing opening passes.

8. An oral-product container, comprising:
   a) a plurality of breath fresheners contained therein for breath freshening purposes;
   b) a mirror for visage freshening purposes and unmovably fixed to said container:
   c) a lid for covering said mirror, said lid being mounted on said container in a manner to move relative to the mirror;
   d) wherein said container includes a dispensing opening configured to dispense a few breath fresheners at a time, said dispensing opening having an area less than about 10 times the size of said breath fresheners.

9. The container of claim 8, wherein said mirror is supported upon an insert within said container.

10. The container of claim 9, wherein said insert is formed from a molded plastic.

11. The container of claim 10, wherein said container is formed with a metal.

12. The container of claim 8, wherein said mirror is supported upon a wall within said container that is not an external wall of said container.

13. The container of claim 12, wherein said wall upon which said mirror is supported is an outer wall of a plastic insert and wherein said container is a metal container that encases said insert when said lid is closed.

14. The container of claim 8, wherein said lid is configured to move between a closed state in which said lid obstructs both said mirror and a dispensing opening and an open state in which said lid exposes both said mirror and said dispensing opening.

15. An oral-product container, comprising:
   a) a plurality of breath fresheners contained therein for breath freshening purposes;
   b) a mirror for visage freshening purposes unmovably fixed to said container;
   c) a lid for covering said mirror in a closed state and for exposing said mirror in a open state;
   d) a product dispensing opening in said container, wherein said mirror is fixedly positioned with respect to said product dispensing opening so as not to move relative thereto.

16. The container of claim 15, wherein said mirror is supported upon an insert within said container.

17. The container of claim 16, wherein said insert is formed from a molded plastic.

18. The container of claim 15, wherein said mirror is supported upon a wall within said container that is not an external wall of said container.

19. The container of claim 18, wherein said wall that supports said mirror is an outer wall of a plastic insert and wherein said container is a metal container that surrounds said insert when said lid is dosed.

20. The container of claim 15, wherein said lid is configured to move between a dosed state in which said lid obstructs both said mirror and a dispensing opening and an open state in which said lid exposes both said mirror and said dispensing opening.

21. The container of claim 15, wherein said lid is mounted for lateral sliding movement between a closed state and an open state.

22. The container of claim 15, wherein said lid is mounted for pivotal movement between a closed state and an open state.

* * * * *